US008657817B2

(12) United States Patent
Fischer et al.

(10) Patent No.: US 8,657,817 B2
(45) Date of Patent: Feb. 25, 2014

(54) HF SURGICAL INSTRUMENT

(75) Inventors: Klaus Fischer, Nagold (DE); Erich Werner, Wannweil (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1720 days.

(21) Appl. No.: 11/718,418

(22) PCT Filed: Nov. 7, 2005

(86) PCT No.: PCT/EP2005/011891
§ 371 (c)(1),
(2), (4) Date: May 2, 2007

(87) PCT Pub. No.: WO2006/050888
PCT Pub. Date: May 18, 2006

(65) Prior Publication Data
US 2008/0208185 A1    Aug. 28, 2008

(30) Foreign Application Priority Data

Nov. 11, 2004   (DE) .......................... 10 2004 054 575

(51) Int. Cl.
*A61B 18/14*   (2006.01)
(52) U.S. Cl.
USPC ................................. 606/42; 606/39; 606/34
(58) Field of Classification Search
USPC ............................. 606/37–41, 32–34, 45–48
See application file for complete search history.

(56) References Cited

U.S. PATENT DOCUMENTS

| 4,860,745 | A | | 8/1989 | Farin et al. |
| 5,422,567 | A | * | 6/1995 | Matsunaga .................... 324/142 |
| 5,976,128 | A | * | 11/1999 | Schilling et al. ................ 606/34 |
| 2001/0044625 | A1 | * | 11/2001 | Hata et al. ........................ 606/41 |

FOREIGN PATENT DOCUMENTS

| DE | 3530335 A1 | 3/1987 |
| DE | 3942998 A1 | 4/1991 |
| DE | 41 26 609 A1 | 2/1993 |
| DE | 20014128 U1 | 4/2001 |
| EP | 253012 A1 | 1/1988 |
| JP | 63-24933 A | 2/1988 |
| JP | 2000-201944 A | 7/2000 |
| WO | 03/005918 A1 | 1/2003 |

* cited by examiner

*Primary Examiner* — Michael Peffley
*Assistant Examiner* — Samantha Good
(74) *Attorney, Agent, or Firm* — Dickstein Shapiro LLP

(57) ABSTRACT

The invention relates to an HF surgical instrument for treating, in particular for cutting and coagulating, biological tissue by means of an HF current. The HF surgical instrument comprises an HF generator for supplying an HF current to a cutting electrode and at least one control device for interrupting an HF current circuit. The control device comprises a current monitoring device, which detects the amplitude of the HF current and then generates a first switch-off signal when the HF current decreases over a defined period of time and/or the HF current falls below a threshold value characterizing a state of the treated tissue, as well as an arc monitoring device, which generates a second switch-off signal when an arc is formed between the cutting electrode and the tissue. The control device is configured in such a way that the HF current circuit is interrupted in response to the first switch-off signal or the second switch-off signal.

12 Claims, 3 Drawing Sheets

HF SURGICAL INSTRUMENT

CROSS-REFERENCE TO RELATED APPLICATIONS

This application is a Section 371 of International Application No. PCT/EP2005/011891, filed Nov. 7, 2005, which was published in the German language on May 18, 2006, under International Publication No. WO 2006/050888 A1 and the disclosure of which is incorporated herein by reference.

BACKGROUND OF THE INVENTION

The invention relates to an HF surgical instrument for treating, in particular for cutting and coagulating, biological tissue by means of an HF current.

High-frequency surgery has been used for many years in both human and veterinary medicine to coagulate and/or to cut biological tissue. Here, with the aid of suitable electrosurgical instruments, high-frequency current is passed through the tissue being treated, causing it to alter due to protein coagulation and dehydration. In the course of this, the tissue constricts in such a way that the vessels occlude and bleeding is staunched. A subsequent increase in the current density causes explosive vaporization of the tissue fluid and tearing of the cellular membranes, completely cutting the tissue in two. Procedures of this kind have the advantage over a purely mechanical cut of affecting a haemostasis of the cut edges.

To carry out a coagulation and/or cutting procedure, HF surgical instruments are used which have inter alia an HF generator for producing a high-frequency voltage and, with that, the high-frequency alternating current, as well as a control unit for switching the HF generator on and off and for interrupting an HF current circuit. In addition, input and output connections are provided for connecting external switches and various electrosurgical instruments.

After a coagulating procedure and, in particular, after a cutting procedure, the HF generator should be switched off or the HF current circuit should be interrupted at a suitable point in time, so that too severe and also unnecessary damage to the treated tissue is avoided. Hence it is essential to clearly identify the individual phases in order to interrupt the current circuit at a suitable point. As the electrosurgical operations are in the millisecond range, the optimum end point of an electrosurgical procedure is hardly encountered by manual switching. In this respect, known HF surgical instruments prefer the control device referred to above, to which, for example, an arc monitor is assigned. The arc monitor recognizes for instance, from the occurring higher harmonic frequencies or also from non-harmonic frequencies of the driving voltage or the HF current, that an arc has ignited between the active electrode/the active electrodes and the tissue. The criterion of arc recognition serves to detect an incipient cutting procedure. So that the cutting procedure recognized by means of the arc can be continued, the procedure is often maintained for a predefined period of time by means of a timer. However, depending on the limiting factors affecting the course of the operation, such as tissue conditions or also the handling of the electrosurgical instrument, the transition, i.e. the exact onset of cutting, cannot be precisely determined because the arc is only recognized with a delay.

An HF surgical instrument for cutting and coagulating, which has inter alia an arc monitoring device of the type described above, for controlling a cutting phase, for example, is known from DE 35 30 335 C2. The cutting procedure occurs here in time intervals, the duration of which can be adjusted and the start of which is triggered by an arc. The termination of an individual cutting phase occurs in each case at the end of a time interval. Accordingly, individual cutting impulses with so-called fractioned cutting are controlled by means of the arc monitor in conjunction with a timer, wherein the foregoing problems occur. It is not guaranteed that the arc is immediately recognized at a first appearance. Hence the timeframe for a cutting impulse may be too great, for example, and there is too much cutting. If the cutting impulse should fail briefly, however, there may possibly be no cutting action and the tissue is, at best, coagulated. Here, too, limiting factors affecting the course of the operation, such as tissue conditions or also the handling of the electrosurgical instrument, are not taken into account, and the cutting phase is in fact terminated, irrespective of external factors and irrespective of a cutting procedure, solely on the basis of the end of the defined period of time.

BRIEF SUMMARY OF THE INVENTION

Thus the object of the invention is to provide an HF surgical instrument of the kind initially referred to in such a way that cutting performance can be improved.

According to the present invention there is provided an HF surgical instrument for treating, in particular for cutting and coagulating, biological tissue by means of an HF current, wherein the HF surgical instrument comprises an HF generator for supplying an HF current to a cutting electrode and at least one control device for interrupting an HF current circuit. The control device has a current monitoring device, which detects the amplitude of the HF current and then generates a first switch-off signal when the HF current decreases over a defined period of time and/or the HF current falls below a threshold value characterizing a state of the treated tissue. In addition, the control device has an arc-monitoring device which generates a second switch-off signal when an arc is formed between the cutting electrode and the tissue. The control device is configured in such a way that the HF current circuit is interrupted in response to the first switch-off signal or the second switch-off signal.

The basis of the invention is that the actual onset of a cutting procedure is detected and thus every cutting action is taken into account.

In cutting mode, the voltage is in fact sufficiently high that, with sufficiently strong coagulation of the tissue and an associated incipient vapor phase, the possibility of the arc formation already exists at the start of the vapor phase. The cutting process thus begins with the onset of the vapor phase, wherein an arc cannot as yet be recognized, for example, due to signal noise. Depending on the tissue structure, the embodiment of the electrosurgical instrument, the latter's handling and other limiting factors affecting the operation, the vapor phases differ in particular with respect to their length. With very short vapor phases, the delayed recognition is negligible; the recognizable emergence of an arc would guarantee a sufficiently precise detection of the onset of a cutting phase. With very long vapor phases, the cutting action already occurring there cannot remain undetected, however. In this respect, a current monitor is used here for the timely recognition of the cutting phase.

This means that now, because of the control device, ultimately—according to this invention—the cutting action is detectable either by means of the current monitor or the arc monitor. Thus, either any possibly emerging recognizable arc is detected or, however, a characteristic drop in current is detected. To detect the drop in current, the flow of the current is tracked over the defined period of time, ideally by detecting the amplitude or the amplitude progression, in such a way that the true drop in current relative to local maxima and minima emerges and can be recognized. Thus, to detect the drop in current, for example, the averaged current strength may be observed within the sufficiently large time interval (sliding average), in order to reduce the difference between local maxima and minima. The averaging reduces the probability of an incorrect interruption of the HF current circuit by the current monitoring device due to a false interpretation of the curve progression. The reduction of the difference between the local maxima and minima likewise makes possible a more precise recognition of the threshold value that may be achieved.

In a first preferred embodiment, the control device transmits the first switch-off signal or the second switch-off signal to the HF generator, causing the latter to switch off and interrupt the HF current circuit. Thus a particularly simple and reliable embodiment for interrupting the current circuit is realized.

In a further preferred embodiment, at least a first signal processing device is provided, to which the first switch-off signal or the second switch-off signal can be supplied, wherein the first signal processing device transmits the particular switch-off signal as a switch-on signal to the HF generator, causing this to switch on and close the HF current circuit. Since any cutting impulse is simultaneously terminated with the switching off of the HF generator and, accordingly, the interrupting of the HF current circuit, the switch-off signal may be used to initiate a next cutting impulse. That is to say, the switch-off signal is supplied again as a switch-on signal from the first signal-processing device to the HF generator, causing this to switch on again. This is particularly advantageous with fractioned cutting, i.e. in intermittent cutting mode, where a complete severing of tissue is only achieved by a succession of several cutting impulses. Thus the surgeon may concentrate on the procedure while the control of the cutting phase occurs automatically.

A further preferred embodiment provides for at least a first timer device being assigned to the at least first signal processing device, so that the first signal processing device controls the HF generator in such a way that the switching on of the HF generator occurs after a defined period of time. This allows pause intervals of any length to be provided between the individual cutting impulses in order to guarantee, for example, that the operating field cools down again.

In one preferred embodiment, an evaluating device, which detects the amplitude of the HF current or, very generally, the flow of the current by calculating the mean value from a defined number of measured values last read in each case, is assigned to the current monitoring device. That is to say, permanent detection of amplitude values of the HF current or, very generally, of current values and a permanent averaging (sliding average) occur. Thus either the threshold value or a drop in the HF current over a defined period of time is calculated. The averaging reduces the possibility of an incorrect interruption of the HF current circuit by the current monitoring device due to a false interpretation of a curve progression. That is to say, the prospect of interpreting local maxima or minima, i.e. noise, incorrectly is particularly avoided.

In a further preferred embodiment, a second timer device, which maintains a cutting mode for a defined period of time after generating the first switch-off signal, is assigned to the current monitoring device. Thus the cutting mode may be automatically sustained for a desired period of time, without the surgeon having to intervene in the sequence. The period of time may already be determined prior to the procedure, for example. Obviously, it is possible to interrupt the cutting mode when the switch-off signal is generated.

One solution according to the invention provides for a detection device, which detects higher harmonic frequencies and/or non-harmonic frequencies of the HF current as a characteristic frequency of the presence of the arc, being assigned to the arc-monitoring device. Since an arc acts as a non-linear resistance, an alternating current flowing through the arc is distorted in such a way that higher harmonic or also non-harmonic frequencies of the HF current are formed. Through the detection of these frequencies, the recognition of an arc is realized in the simplest way.

Alternatively, it is possible to provide a device by means of which the arc is optically recognized and a corresponding signal is generated. This allows the arc to be identified in a simple manner.

One preferred embodiment provides for a third timer device, which maintains a cutting mode for a defined period of time after recognizing the arc, being assigned to the arc-monitoring device. Since the arc monitoring device only becomes active according to the invention when the current monitoring device fails to first interrupt the HF current circuit and the recognition of the arc gives a clear instruction to start a cutting phase, the timer device allows any defined cutting length, which then corresponds to a true cutting length, to be provided in a simple manner.

One advantageous realization of the instrument consists in providing at least a second signal processing device to which the first switch-off signal or the second switch-off signal can be supplied, wherein the second signal processing device controls an optical and/or acoustic indicator means by means of the first switch-off signal or the second switch-off signal in such a way that the interruption of the HF current circuit in response to the first switch-off signal or the second switch-off signal is indicated for user guidance. The indicator means makes it is possible to track a previously charted cutting operation, i.e. previously recorded limiting factors, during the further procedure and thus to both assess tissue structures and adapt the further handling of the electrosurgical instrument to this.

In one preferred embodiment, at least one storage device is provided which stores the switch-off signals generated each time within one procedure for subsequent and/or simultaneous indication of a cutting operation. Thus earlier cutting operations can be called up and the resulting experience used for further procedures.

A further advantageous embodiment provides for the cutting electrode being configured as a loop electrode. Loop electrodes for monopolar cutting are particularly suited to removing polyps or other raised sections of tissue, because these may be gripped and held by means of the loop. Alternatively, it is possible to use bipolar loop electrodes.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
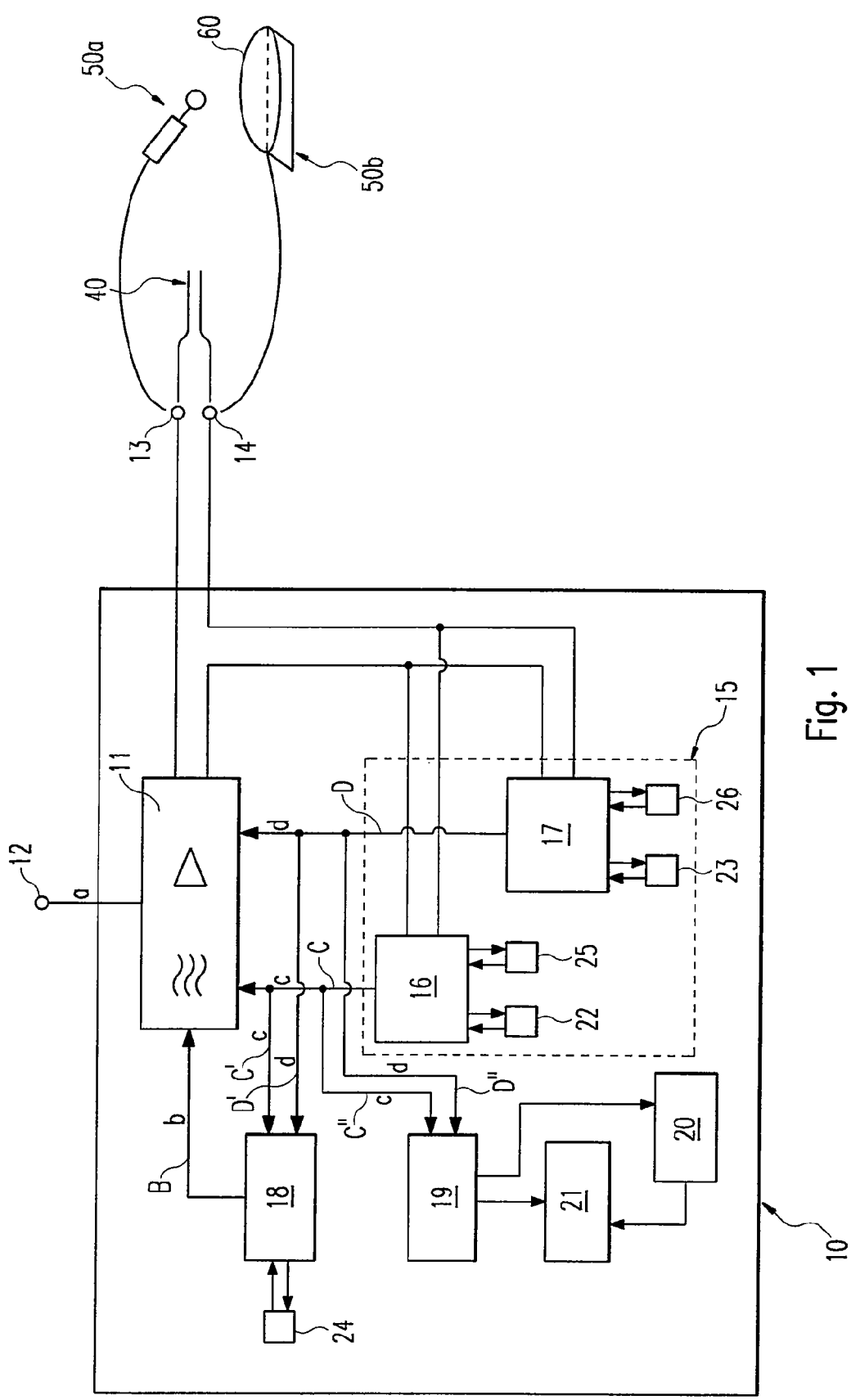
FIG. 1 is a functional block diagram, which represents one embodiment of the HF surgical instrument according to the invention.

In the following description, the same reference numerals are used for the same and equivalent components.

FIG. 1 depicts an embodiment of the instrument according to the invention. Here components of an HF surgical instrument 10 that are essential to explain the invention and other components of an HF surgical arrangement are schematically depicted.

The HF surgical instrument 10 has an input connection 12 for connecting switching devices (not depicted) that have finger and/or foot switches. These switching devices facilitate activation and/or deactivation of the HF current. The switching devices are preferably realized here by means of a computer arrangement. Provided on the HF surgical instrument 10 on the output side are a first output connection 13 and a second output connection 14, to which a bipolar electrosurgical instrument 40 or a monopolar electrosurgical instrument 50a with an associated neutral electrode 50b may be connected. This representation is simplified. With the practical embodiment of an HF surgical instrument, various connections for monopolar or bipolar electrode arrangements are provided for the most part. The neutral electrode is also schematically represented and in a practical application will completely cover a section of body 60 of a patient.

The central part of the HF surgical instrument 10 is a controllable HF generator 11 for generating an HF current or, more accurately, for generating a voltage. The desired current strengths $I_{HF}$ can be defined from the setting of the voltage. The HF generator 11 is connected to a control device 15, wherein the control device 15 has a current monitoring device 16 and an arc-monitoring device 17. The control device 15 is connected into a return circuit from the electrosurgical instrument to the HF generator 11. An evaluating device 22 and a second timer device 25 are assigned to the current monitoring device 16, while a detection device 23 and a third timer device 26 are assigned to the arc-monitoring device 17.

In this embodiment example, a first signal-processing device 18 is provided with an assigned first timer device 24, and a second signal-processing device 19 is provided with an assigned indicator 21. A storage device 20 is connected to the indicator 21 and the second signal-processing device 19.

Figure 2:
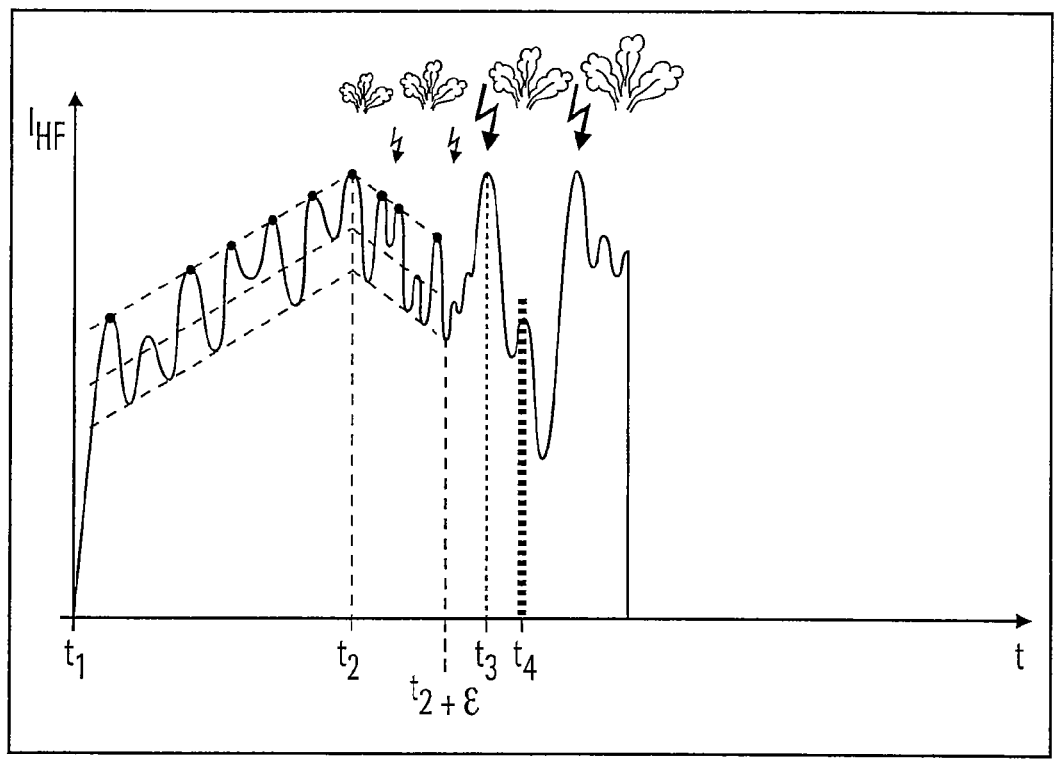
FIG. 2 is a current-time diagram, which depicts the flow of current in a cutting mode with a loosely positioned loop.

The mode of action of the instrument is described below from FIGS. 2 and 3. Here, by way of example, an endoscopic removal of a polyp by means of the monopolar loop electrode 50a is explained. FIG. 2 here depicts a current-time diagram. With this flow of current, the loop 50a is placed loosely around the polyp because there is no danger of the polyp slipping out. A current-time diagram can also be seen in FIG. 3, wherein a flow of current is reproduced for the removal of the polyp with a tightened loop 50a. The strangling of the polyp is necessary if the latter could slip out of the loop 50a as a result of its physical form.

Through actuation of the switching devices, a switch-on signal is applied to the HF generator 11, the HF generator 11 begins operation, and a cutting phase by means of the loop electrode 50a can commence. In practical application, an additional switch-on criterion is for the most part necessary, to activate electrodes on the electrosurgical instrument. This may occur, for example, by means of a further hand switch on the instrument. The HF current is supplied to the tissue being treated, i.e. to the polyp, via the electrode. Since the control device 15, i.e. the current monitoring device 16 and the arc-monitoring device 17 are connected into the return circuit to the HF generator 11, they register an amplitude variation of the HF current or creation of an arc.

According to FIG. 2, the cutting mode is switched on at a point in time t1, and the current begins to flow through the tissue being treated via the loop electrode 50a loosely positioned on the polyp. Owing to the heating of the tissue, the current strength $I_{HF}$ increases up to a point t2. From the point t2 onwards, the tissue begins to coagulate so strongly that a vapor phase sets in. Because of the heat build-up attributable to the HF current, a defined area of tissue is altered or destroyed by protein coagulation and dehydration. The colloidal constituents of tissue in the nominal state first pass here into the gelatinous state, wherein the now gelatinous constituents of tissue then solidify further while fluid escapes; the tissue vaporizes. The resistance of the tissue increases accordingly, causing the current strength $I_{HF}$ to decrease to a point t2+ε due to the declining conductivity of the tissue. The vapor phase between t2 and t2+ε is in this instance, however, extremely short, so that a cutting procedure during this vapor phase hardly makes a difference. Because of the now increasingly developing insulating layer on the tissue, a now recognizable arc will ignite at a point t3. After the arc has been recognized by the arc-monitoring device 17, the latter generates a switch-off signal d. The switch-off signal d is transmitted to the HF generator 11 in this embodiment example by means of a control line D, causing it to interrupt the HF current circuit at a desired point in time, e.g. at point t4, by switching off, for example. Thus the cutting procedure is concluded.

Figure 3:
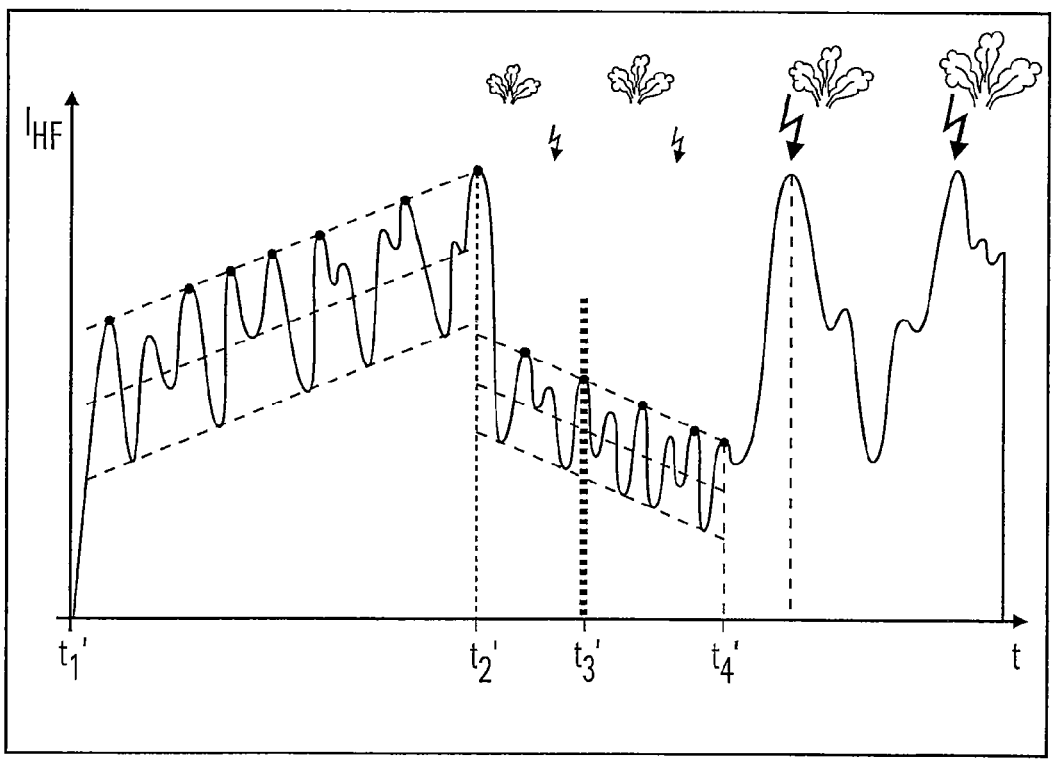
FIG. 3 is a current-time diagram, which depicts the flow of current in a cutting mode with a firmly positioned loop.

As can be seen from FIG. 3, from a point t1' onwards the tissue being treated will also heat up with a strangled polyp until the start of a strong coagulation at a point t2'. In this instance, a characteristic drop in current at point t2'—the start of a vapor phase—can be noted. Already at this point in time, because of a high voltage in cutting mode, arcs will ignite which are not recognized by the arc-monitoring device 17, as already described above. The current monitoring device 16 recognizes the drop in current, however. A switch-off criterion for the current monitoring device 16 is thus, for example, a decreasing HF current average value over a set period of time t2'-t3'.

Alternatively, instead of a defined period of time, it is possible for the current monitoring device to detect a threshold value characterizing a state of the treated tissue, so that this device generates a switch-off signal c once the threshold is reached, for example at t3'. The switch-off signal c is transmitted to the HF generator 11 in both cases by means of a control line C, causing it to interrupt the HF current circuit at a desired point in time, by switching off, for example. Thus the cutting procedure at the point t3' is already concluded before the end of the vapor phase at a point t4'.

It can be ascertained that the arc recognition inter alia is very strongly dependent on the pulling force of the loop on the polyp stalk. Through a greater mechanical pull with a firmly positioned loop, arcs are formed that would be recognized in a clearly delayed manner compared to arcs with a loosely adjusted loop.

The evaluating device 22 assigned to the current monitoring device 16 detects the drop in current over the defined period of time or the threshold value by calculating the average value from a defined number of measured values last read in each case. Thus, ideally, permanent detection of amplitude values of the HF current and permanent averaging are carried out in order to recognize noise from the signal and reduce the probability of an incorrect switching off of the HF generator 11, i.e. an interruption of the HF current circuit by the current monitoring device 16 due to a false interpretation of a curve progression. The averaging should preferably first occur at a predefined point after the start of the readings, so that a recognizable curve progression emerges.

The cutting mode can be maintained for a defined period of time after the start of the cutting phase by means of the second timer device 25. Thus the cutting mode may be automatically sustained for a desired period of time without the surgeon having to intervene in the sequence. The period of time may already be determined prior to the procedure, for example.

The detection device 23 assigned to the arc monitoring device 17 is configured in such a way, for example, that it detects higher harmonic frequencies and/or non-harmonic frequencies of the HF current as a frequency characteristic of the arc. Through the detection of these frequencies, the recognition of an arc is realized in the simplest way.

The third timer device 26 is assigned to the arc-monitoring device 17 and allows the cutting phase to be extended for a desired period of time after the arc has been recognized.

As depicted in FIG. 1, both the first switch-off signal c and the second switch-off signal d can be supplied to the first signal processing device 18 via control lines C', D'. The first signal processing device 18 is configured in such a way that the particular switch-off signal c or d can be transmitted as a new switch-on signal b to the HF generator 11 via a control line B, causing it to switch on again or close the current circuit after the HF current circuit has been switched off or interrupted. This is particularly advantageous with fractioned cutting, i.e. in intermittent cutting mode, where a complete severing of tissue is only achieved by a succession of several cutting impulses. Thus the surgeon may concentrate on the procedure while the control of the cutting phase occurs automatically.

If the first timer device 24 is assigned to the first signal-processing device 18, as provided in this embodiment example, the first signal-processing device 18 will not control the HF generator 11 until after a defined period of time. This allows pause intervals of any length to be provided between the individual cutting impulses in order to guarantee, for example, that the operating field cools down again.

The first switch-off signal c and the second switch-off signal d can likewise be supplied to the second signal processing device 19 via control lines C'', D'', wherein the second signal processing device 19 controls the optical and/or acoustic indicator 21 by means of the first switch-off signal c or the second switch-off signal d in such a way that the switching off of the HF generator 11 or the interruption of the HF current in response to the first switch-off signal c or the second switch-off signal d is indicated for user guidance. The indicator 21 makes it is possible to track a previously charted cutting operation during the further procedure and thus to both assess tissue structures and adapt the further handling of the electrosurgical instrument to this.

Preferably, the particular switch-off signals c, d are stored by means of the storage device 20, to make these available for subsequent analysis from the indicator 21 or also from a printout. The records serve to make resulting experiences useful for further procedures.

Figure 4:
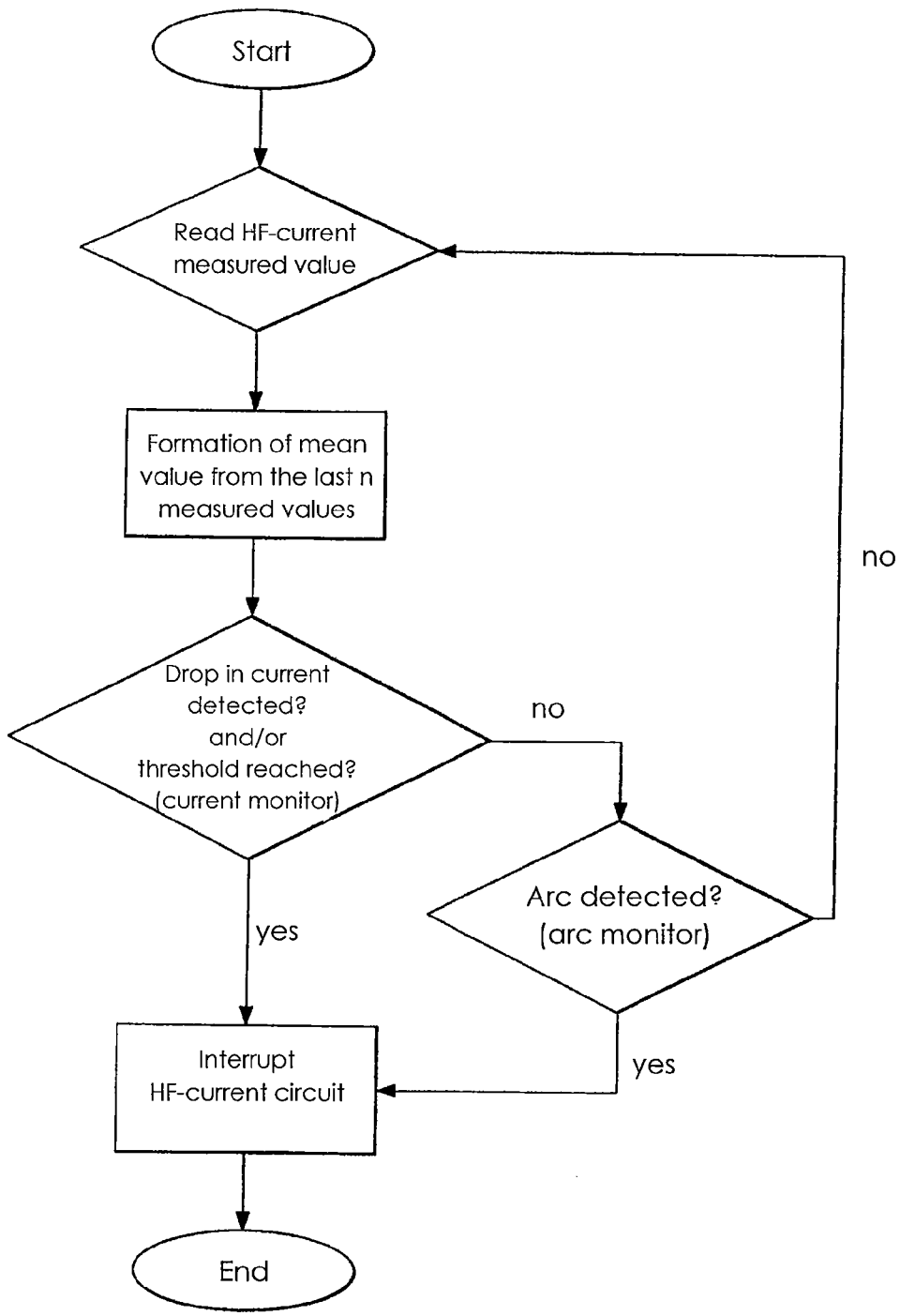
FIG. 4 is a flow chart, which depicts a mode of operation of the HF surgical instrument shown in FIG. 1.

FIG. 4 depicts a flow diagram, which depicts a mode of operation of the HF surgical instrument 10 according to FIG. 1, wherein only essential components, i.e. the current monitoring device 16 and the arc-monitoring device 17, of the HF surgical instrument 10 are included. The flow diagram is represented in a greatly reduced manner, being geared to the characteristics of the either- or relationship between the monitoring devices.

The procedure begins with the reading of measured values of the HF current, wherein the averaging is carried out from the defined number of the last measured values read, in order to detect either the decreasing characteristics of the HF current average over the defined period of time as a first switch-off criterion or the attainment of the threshold value defining the state of the tissue as a first switch-off criterion. On reaching the first switch-off criterion the HF generator 11 is controlled in such a way that it interrupts the HF current circuit, i.e. switches it off in the simplest case. If the first switch-off criterion is not reached, the arc recognition is verified by the arc-monitoring device 17. On detecting an arc, the HF generator 11 switches off or interrupts the HF current circuit. If the arc recognition proves negative, a measured value of the HF current is read and the procedure recommences.

The interruption of the HF current circuit may thus occur, as already described several times, by switching off the HF generator or the current circuit is otherwise interrupted, however, e.g. by means of a switch actuated by the control device.

At this juncture, it should be pointed out that all the parts described above have been claimed for themselves alone and in any combination, in particular the details represented in the drawings, as essential to the invention. Revisions to this are familiar to the man skilled in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A high frequency (HF) cutting and coagulating surgical instrument for cutting and coagulating biological tissue by means of an HF current, comprising:
    a cutting electrode;
    an HF generator for supplying an HF current to said cutting electrode; and
    at least one control device for interrupting an HF current circuit, comprising:
    a current monitoring device, adapted to detect the amplitude of the HF current and to generate a first switch-off signal when as a first switch-off criterion at least one of the following occurs:
       (a) the HF current decreases over a defined period of time; and
       (b) the HF current falls below a threshold value characterizing a state of the treated tissue,
    an arc monitoring device, adapted to generate a second switch-off signal when as a second switch-off criterion an arc is formed between the cutting electrode and the tissue, and
    a timer to delay either the first or second switch-off signals for a time period after they have been detected, wherein
    the control device being designed to detect an incipient cutting action during a vapor phase of a tissue treatment procedure
    by detecting whether the first switch-off criterion is reached and if the first switch-off criterion is not reached, the second switch-off criterion is verified by the arc monitoring device, so that the HF circuit is interrupted in response to the first switch-off signal or the second switch-off signal after the time period to allow cutting action by the HF circuit.

2. The HF surgical instrument according to claim 1, wherein said control device transmits the first switch-off signal and the second switch-off signal to the HF generator, causing the generator to switch off and to interrupt the HF current circuit.

3. The HF surgical instrument according to claim 1, comprising:
at least a first signal processing device to which the first switch-off signal and the second switch-off signal are supplied, and which is adapted to transmit the particular switch-off signal as a switch-on signal to the HF generator, causing the generator to switch on and to close the HF current circuit.

4. The HF surgical instrument according to claim 3, wherein the timer is assigned to at least the first signal processing device so that the first signal processing device controls the HF generator in such a way that the switching on of the HF generator occurs after a predetermined period of time.

5. The HF surgical instrument according to claim 1, comprising:
an evaluating device, which detects the amplitude of the HF current by calculating the mean value from a predetermined number of last read measured values, and which is assigned to the current monitoring device.

6. The HF surgical instrument according to claim 1, wherein the timer
maintains a cutting mode of the instrument for a defined period of time after generation of the first switch-off signal, and is assigned to the current monitoring device.

7. The HF surgical instrument according to claim 1, comprising:
a detection device, which detects at least one of higher harmonic frequencies and non-harmonic frequencies of the HF current as a characteristic frequency of the presence of an arc, and which is assigned to the arc-monitoring device.

8. The HF surgical instrument according to claim 1, wherein the timer
maintains the cutting mode of the instrument for a defined period of time after formation of the arc, and is assigned to the arc monitoring device.

9. The HF surgical instrument according to claim 1, comprising:
a signal processing device to which at least one of the first switch-off signal and the second switch-off signal is supplied, and which is adapted to control an indicator by means of the supplied switch-off signal in such a way that the interruption of the HF current circuit in response to the supplied switch-off signal is indicated for user guidance.

10. The HF surgical instrument according to claim 1, comprising:
at least one storage device which stores the switch-off signals generated each time within one procedure for subsequent or simultaneous indication of a cutting operation.

11. The HF surgical instrument according to claim 1, wherein said cutting electrode is configured as a loop electrode.

12. A high frequency (HF) cutting and coagulating surgical instrument for cutting and coagulating biological tissue by means of an HF current, comprising:
a cutting electrode;
an HF generator for supplying an HF current to said cutting electrode;
at least one control device for interrupting an HF current circuit, comprising:
a current monitoring device, adapted to detect the amplitude of the HF current and to generate a first switch-off signal;
an arc monitoring device, adapted to detect an electric arc between the cutting electrode and the tissue and to generate a second switch-off signal; and
a timer to delay either the first or second switch-off signals for a time period after they have been detected, wherein
the control device detects a cutting action during a tissue treatment procedure by determining if the current monitoring device has generated a first switch-off signal and if no first switch-off signal has been generated, determining if the arc monitoring device has generated a second-switch-off signal so that the HF circuit is interrupted in response to the first switch-off signal or the second switch-off signal after the time period to allow cutting action by the HF circuit.

* * * * *

UNITED STATES PATENT AND TRADEMARK OFFICE
CERTIFICATE OF CORRECTION

PATENT NO. : 8,657,817 B2  Page 1 of 1
APPLICATION NO. : 11/718418
DATED : February 25, 2014
INVENTOR(S) : Fischer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1858 days.

Signed and Sealed this

Twenty-ninth Day of September, 2015

Michelle K. Lee
*Director of the United States Patent and Trademark Office*